(12) United States Patent
Dinkler

(10) Patent No.: US 6,557,195 B2
(45) Date of Patent: May 6, 2003

(54) HINGED ADAPTOR ASSEMBLY FOR RADIOLUCENT TABLE EXTENSION

(75) Inventor: Charles E. Dinkler, Cincinnati, OH (US)

(73) Assignee: Ohio Medical Instruments Company, Inc., Cincinnati, OH (US)

( * ) Notice: Subject to any disclaimer, the term of this patent is extended or adjusted under 35 U.S.C. 154(b) by 0 days.

(21) Appl. No.: 09/928,837

(22) Filed: Aug. 13, 2001

(65) Prior Publication Data
US 2002/0032927 A1 Mar. 21, 2002

Related U.S. Application Data

(63) Continuation of application No. PCT/US00/03639, filed on Feb. 11, 2000
(60) Provisional application No. 60/119,686, filed on Feb. 11, 1999.

(51) Int. Cl.[7] .............................................. A61G 13/12
(52) U.S. Cl. ........................ 5/601; 5/622; 5/638; 5/632
(58) Field of Search ........................... 5/601, 622, 630, 5/632, 637, 638, 643, 658, 661

(56) References Cited

U.S. PATENT DOCUMENTS

| 5,233,713 | A | * | 8/1993 | Murphy et al. ........ 250/363.02 |
| 5,276,927 | A | | 1/1994 | Day |
| 5,317,771 | A | * | 6/1994 | Cook ......................... 128/845 |
| 6,003,174 | A | | 12/1999 | Kantrowitz |

FOREIGN PATENT DOCUMENTS

| EP | 0104591 | 4/1984 |
| WO | WO 9521597 | 8/1995 |
| WO | WO 9911176 | 3/1999 |

* cited by examiner

Primary Examiner—Heather Shackelford
Assistant Examiner—Fredrick Conley
(74) Attorney, Agent, or Firm—Wood, Herron & Evans, LLP

(57) ABSTRACT

An advantageous interoperative system includes a scanner [20] with an enclosed scanning zone, an image guided system [24] operatively connected to the scanner [20], a surgical table [22] having a radiolucent member [228] attached to one end thereof with a radiolucent support [264] held near an outboard end [236] of the radiolucent member [228] by a radiolucent adaptor assembly [210], the radiolucent adaptor assembly [210] being hingedly connected to both the radiolucent member [228] and the radiolucent support [264]. The table [22] and the radiolucent member [228] attached thereto are movable relative to the scanner [20] to locate the radiolucent member [228] and the head of a patient supported thereon within the scanning zone, to facilitate interoperative scans. The two spaced hinged connections of the radiolucent adaptor assembly [210] promote versatility for the surgeon in positioning the radiolucent member [228] and the patient stabilization device [272 or 280] within the scanning zone. The patient stabilization [272, 280] device may be a radiolucent skull clamp [280] or a radiolucent horseshoe headrest [272], and the radiolucent skull clamp [280] and radiolucent horseshoe headrest [272] are mounted on supports [266, 278] which interchangeably connect to the radiolucent adaptor assembly [210].

15 Claims, 9 Drawing Sheets

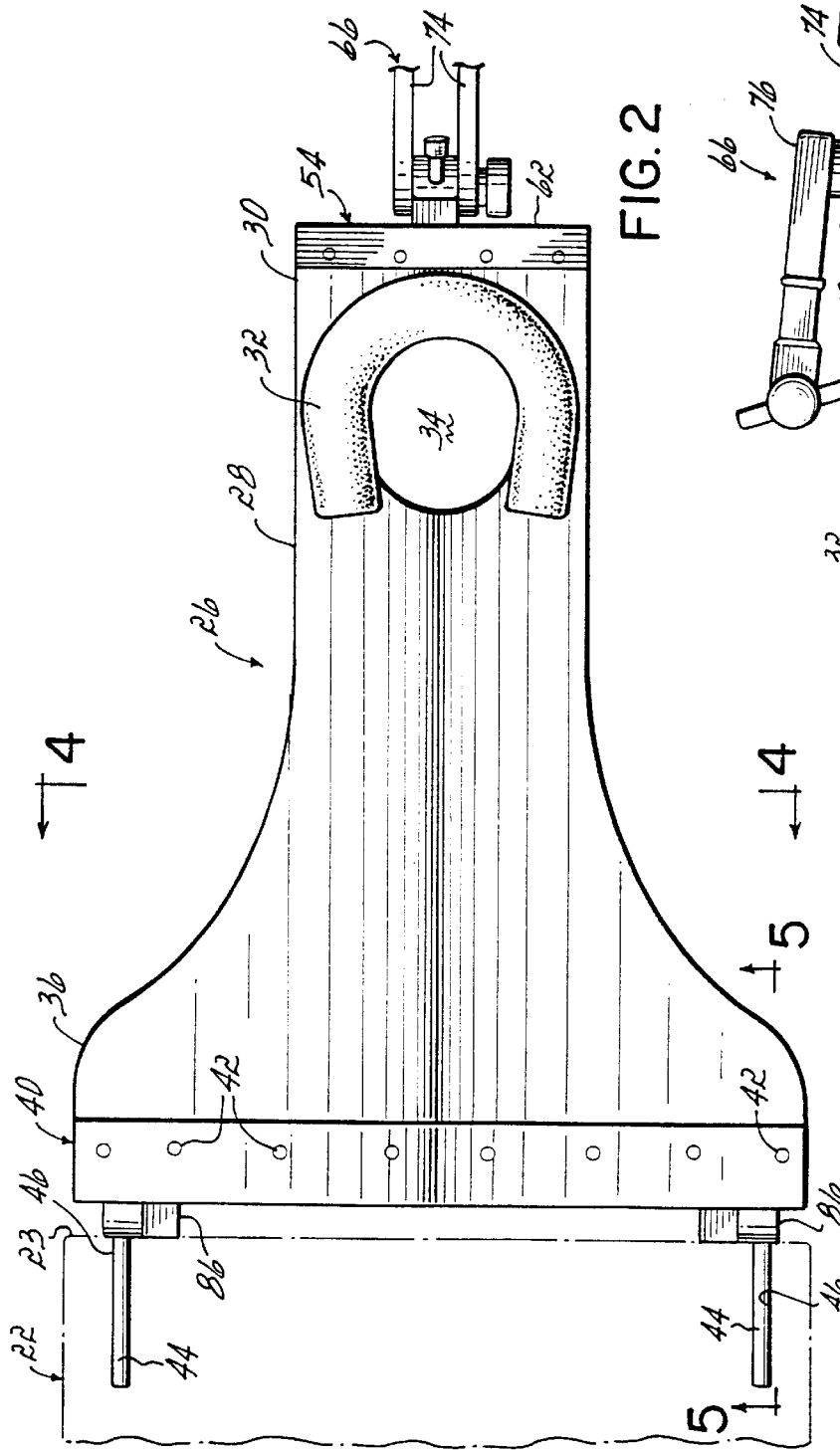

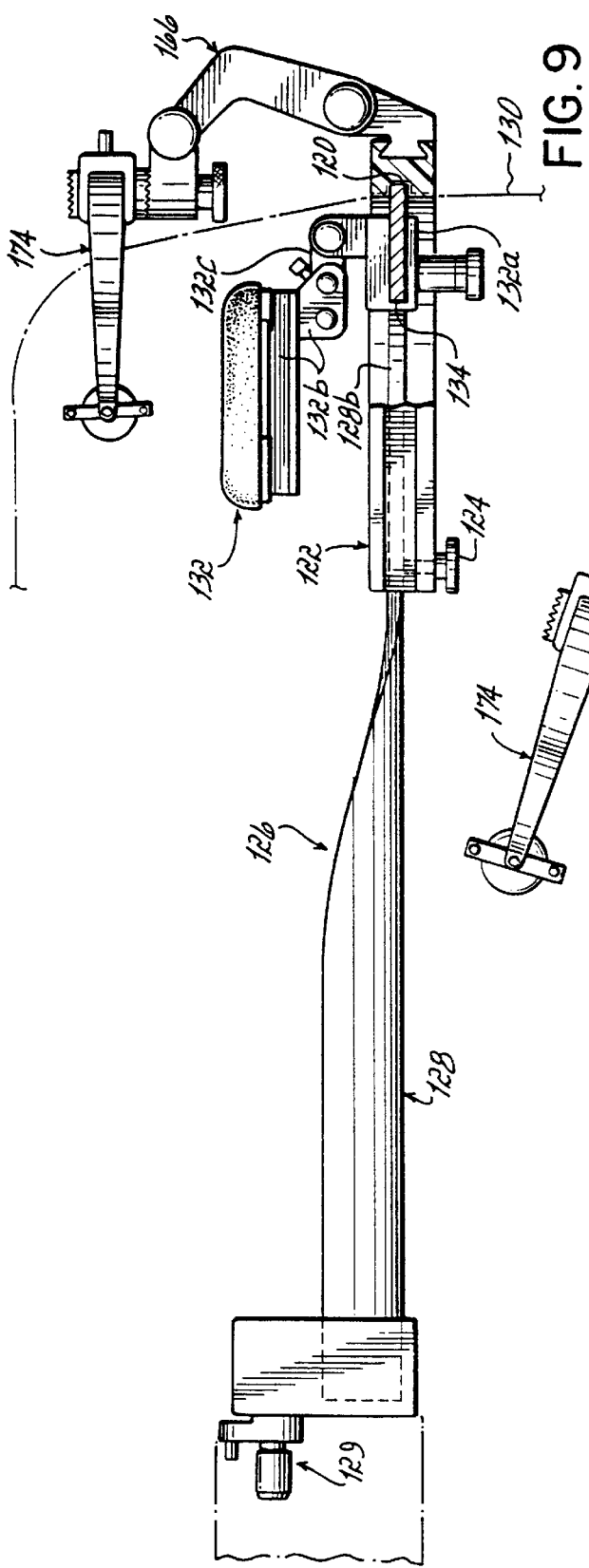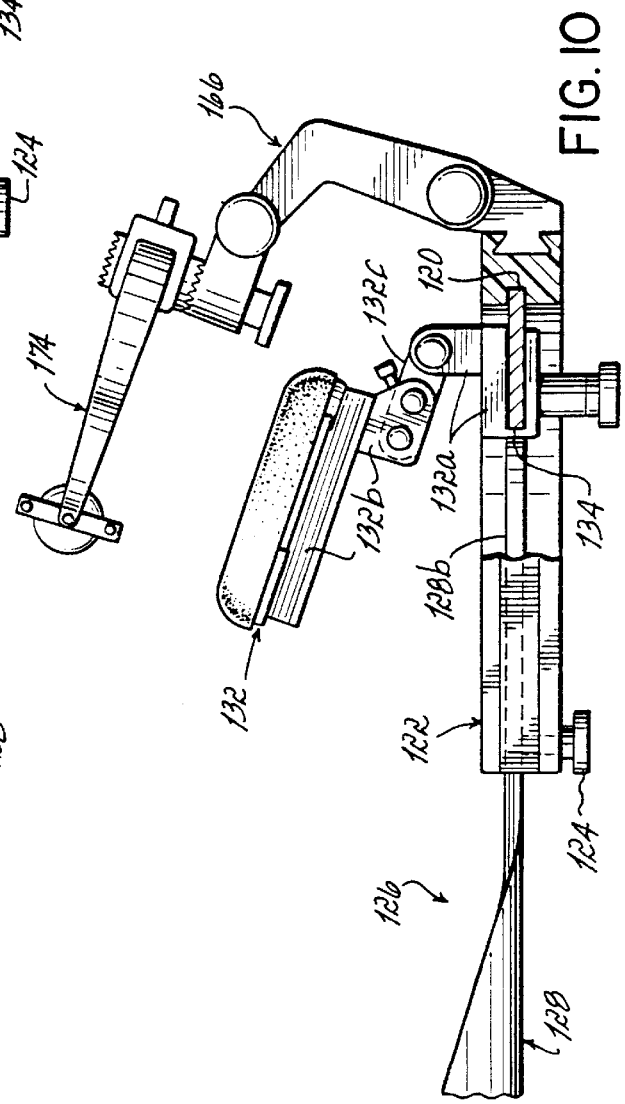

HINGED ADAPTOR ASSEMBLY FOR RADIOLUCENT TABLE EXTENSION

This application is a continuation of PCT Application No. PCT/US00/03639, entitled "Hinged Adaptor Assembly For Radiolucent Table Extension," filed on Feb. 11, 2000, which in turn claims priority to U.S. Provisional Application Ser. No. 60/119,686, filed on Feb. 11, 1999.

FIELD OF THE INVENTION

This invention relates to surgical tables and more particularly, to an improved radiolucent table extension and radiolucent adaptor assembly which facilitates interoperative scanning.

BACKGROUND OF THE INVENTION

With current medical practices, it is common for a patient to undergo a diagnostic scanning procedure, which is normally performed in a separate suite containing the scanning machine and dedicated to scanning procedures. The scanning machine may be a CT, MRI, or other scanning device. Thereafter, the scan data is utilized in a surgical planning process, which conventionally takes place at a location, for example, an office or an operating room. In some surgical procedures, the scanning data is utilized with a system for post processing the scan data acquired during imaging. Further, the imaging system may be located in a surgical suite, and the surgical planning performed before and during surgical procedure utilizing the imaging system and scan data.

During the scanning procedure, the patient must maintain a perfectly still and motionless posture, and while most often, the patient simply lies on a scanning support table, in some situations, the patient maybe supported in the desired scanning position with pads, straps or other supports. Further, the support on which the patient rests is normally radiolucent, that is, transparent to the scanning device, so that the support does not compromise the utility of the scanned image. Further, the patient support used for scanning normally translates with respect to the imaging device. Translation of the patient support permits the patient to be moved into the scanning field or zone of the scanning machine.

After the scanning process is completed, often the patient is then moved to an operating room which requires either that the patient walk, or be carried, for example, by transferring the patient from the scanning table to an operating table. Alternatively, as illustrated in U.S. Pat. No. 5,475,884, the patient may be supported on a portable support plate, which is easily moved between the scanning table and the operating table. The scan data is often used in a post processing imaging system for surgical planning purposes both prior to and during surgery. If during or after a surgical process, it is desired to scan a patient again, the patient must be moved from the operating room to the scanning suite, transferred to and from the operating table to the scanning table, and after scanning, transferred back to the operating table and returned to the operating room. The above process is cumbersome, time consuming and potentially risky for the patient.

Some newer scanning machines are substantially reduced in size. One such machine is shown in FIGS. 2 and 3 of U.S. Pat. No. 5,499,415, which show an annular-shaped scanner mounted on a wheel-supported frame, to enable the scanner to be used at multiple sites. Consequently, such scanning machines do not require their own suite or room, but instead, they may be used within the operating suite itself. Thus, in an operating room, the patient may be scanned; the surgical planning performed; an operative procedure executed; and the patient scanned again to determine the current status of the operative procedure. Based on the new scanned images obtained from the one or more "interoperative" scans, the operative procedure can be continued and the above process repeated as necessary.

A limitation of the current state-of-the-art is that the posture of the patient during the scanning process is often different from the patient's posture during surgery. If a patient is positioned in one posture on a scanning table during the scanning process, and then is moved to an operating table, that motion of the patient may cause the position of the target to change with respect to the body surface. During surgery, this problem is compounded by tissue shifts attendant to the opening of body cavities, removal of body fluid or tissues and tissue retractions. Thus, while such motion may be small, any motion of the target will reduce or compromise the utility of the preoperative scan data.

The solution to these problems is to scan the patient in the operating room during surgery while the patient is maintained in the surgical posture, and further, to make successive interoperative scans, as necessary, while still holding the patient in the same surgical posture.

While current scanning tables are radiolucent and provide a translation to move the patient into the scanning machine, such scanning tables do not have the accessories required to attach, support and stabilize surgical instrumentation and to properly support the patient's body in the desired surgical posture. Further, while surgical, or operating tables contain numerous accessories and couplings to which surgical instrumentation may be attached and supported, most operating tables are not compatible with scanning instrumentation. Thus, as presently known, scanning tables cannot be used as operating tables, and generally, operating tables are inappropriate for use as scanning tables.

It is an object of this invention to overcome the above-described limitations in the prior art, by facilitating the function of supporting a patient in a desired position in a manner which readily accommodates successive surgical or scanning procedures.

It is another object of the invention to optimize versatility in the supporting of a patient in a desired position which accommodates interoperative scans.

SUMMARY OF THE INVENTION

The present invention achieves the above-stated objectives with a radiolucent table extension that connects to a surgical table and permits a patient to be positioned on the table in a posture suitable for successive surgical or scanning procedures, the head and the upper torso of the patient supported on the table extension, a radiolucent adaptor assembly hingedly connected to the radiolucent table extension and a radiolucent support, of a type which holds either a radiolucent horseshoe headrest or a radiolucent skull clamp, hingedly connected to the radiolucent adaptor assembly. The present invention represents an improvement in versatility over the structure shown and described in U.S. patent application Ser. No. 08/922,969, entitled "Radiolucent Table Extension and Method," which is expressly incorporated by reference herein, in its entirety.

The radiolucent table extension is cantilevered from one end of the surgical table and it is shaped so that it may be moved in a relative manner into a toroidal shaped scanning zone of an upright annular scanning machine. This permits the patient to be scanned in the desired surgical posture. The radiolucent table extension and the radiolucent adaptor assembly of this invention are especially useful for those procedures in which it is desirable to maintain the patient in a desired position during successive scanning or surgical procedures.

By operatively connecting the toroidal scanner to an imaging system, so that the imaging system may store data representative of scans of the patient taken in the scanning zone, and by supporting the patient with the extension and the hingedly connected adaptor, and fixing the position of the patient with the horseshoe headrest or the skull clamp hingedly connected to the adaptor, the present invention optimizes versatility in the positioning of a patient during successive scans, thereby assuring the accuracy of the scanned data. This helps the surgeon to know almost immediately whether the surgical procedure accomplished its objective, or whether continutation of the surgical procedure may be necessary.

According to the principles of the present invention and in accordance with the preferred embodiments, a radiolucent table extension has a first inboard end adapted to be attached to one end of a surgical table. The table extension includes a contoured radiolucent member designed to support an upper torso and head of a patient with the rest of the patient's body being further supported by an adjacently located surface of the table. The member has a sufficiently narrow width to permit it to be extended, in cantilever fashion, into a scanning zone of portable CT scanning system. A second, or outboard end of the radiolucent table extension hingedly connects to a radiolucent adaptor assembly, which preferably comprises two spaced radiolucent adaptor subassemblies hingedly connected along a first connection axis to spaced collars located at the outboard end of the radiolucent member. An arcuate cutout resides between the two spaced collars. This cutout advantageously defines an opening between the extension and the radiolucent support to accommodate surgical tubing. Likewise, a radiolucent support also has two spaced collars aligned along a second connection axis, and the radiolucent support hingedly connects to the radiolucent adaptor assembly along a second connection axis. The two connection axes are parallel, and if desired they may reside in the same vertical plane. The radiolucent support is adapted to support at least one cranial stabilization device, typically either a radiolucent skull clamp or a radiolucent horseshoe headrest.

The radiolucent adaptor assembly actually comprises two spaced adaptor subassemblies. Each radiolucent adaptor subassembly includes opposing interior and exterior pieces which are tightenable, via a threaded adjustment knob, into rigid engagement with the spaced table extension collars and the spaced support collars. Each of the interior and exterior pieces has locator pins in alignment with the first and second connection axes. Along each connection axis, the locator pins extend into the respective collar with a slip fit. The locator pins provide the hinged connection between the radiolucent table extension and the radiolucent adaptor along the first connection axis and the hinged connection between the radiolucent support and the radiolucent adaptor along the second connection axis. Tightening of the adjustment knob effectively moves the interior and exterior pieces horizontally toward each other to engage the outer ends of the collars, preferably via corresponding serrated, or starburst surfaces, thereby to achieve rigid holding. Thus, even though there is hinged capability along two spaced axes, the radiolucent support is locked in place via actuation of knobs residing on a single axis.

The hingedly connected radiolucent support is adapted to support at least one patient stabilization device, typically either a radiolucent skull clamp or a radiolucent horseshoe headrest. When using a radiolucent skull clamp, the radiolucent support comprises a radiolucent bracket which supports a ninety degree radiolucent intermediate connector which in turn holds the radiolucent skull clamp. The radiolucent bracket and the radiolucent intermediate connector connect along a dovetail slot, to enable the radiolucent skull clamp to be slidably located at a desired position relative to the longitudinal axis of the table extension, as may be desired in certain situations.

When the patient stabilization device is a horseshoe headrest, the radiolucent support is a U-shaped panel bearing an upstanding slide mount oriented transverse to the longitudinal direction of the table extension. The radiolucent horseshoe headrest comprises two separate arcuate halves which slidably attach to the slide mount, to form a U-shape for holding the head of the patient.

The U-shaped panel combines with the arcuate cutout region at the outboard end of the table extension to form an enclosed oval, which is advantageous for certain procedures wherein the patient must be positioned face down. In this arrangement the radiolucent adaptor assembly represents, in effect, an intermediately located, double hinge for the entire support assembly attached in cantilever fashion to the surgical table.

Because of the configuration of the radiolucent adaptor assembly, and the configuration of the two different radiolucent supports for holding either a skull clamp or a horseshoe headrest, the present invention provides rigid connection of either configuration with the same adaptor assembly. Thus, the invention greatly simplifies and shortens the time needed for surgical attendants to interchange between a skull clamp set up and a horseshoe headrest set up. Even with a high degree of rigidity and with this ability to easily interchange between two different patient stabilization devices, the present invention also achieves enhanced maneuverability of the patient stabilization device, due to the two hinged connections. According to another aspect of the invention, the adaptor assembly accommodates connection of a horseshoe headrest in an inboard manner, partially surrounding an enclosed oval. The headrest is inboard because the radiolucent plate holding the headrest represents an outermost end of the entire cantilevered structure, and the two hingeable axes reside between this outermost end and the table extension.

Thus, the double-hinged radiolucent adaptor assembly of the present invention optimizes versatility in supportably positioning a patient on a radiolucent table extension, via either a radiolucent skull clamp or a radiolucent horseshoe headrest. With this inventive structure, the patient can be supported on the radiolucent table extension in the desired posture. The patient can then be conveniently scanned before a surgical procedure. After surgery, a subsequent scanning procedures may be performed, if necessary or if desired. Thus, the table extension and adaptor assembly have the advantage of not requiring that the patient be moved with respect to the table extension between successive scanning and surgical procedures.

Moreover with updated scanned images readily available for viewing via the imaging system, the surgeon can review the results of a surgical procedure to determine if a particular operation has been completely successful. For example, if the objective of the surgery was to completely remove a hematoma from the brain, a follow-up scan may enable the surgeon to use the imaging system to determine if the entire hematoma has been removed. If a subsequent scan shows that some of the "target" remains, then the surgeon can continue the surgical procedure, using the imaging system if desired, to achieve 100% removal of the target. Thus, this overall system facilitates successive scanning and surgical procedures, and the radiolucent table extension and the radiolucent adaptor assembly make it possible to use this system more effectively, by assuring accurate and repeatable positioning of the patient.

These and other objects and advantages of the present invention will become more readily apparent from the following detailed description and the drawings.

BRIEF DESCRIPTION OF THE DRAWINGS

FIG. 2 is a top plan view of the radiolucent table extension assembly of FIG. 1. FIG. 3 is a side view in elevation of the radiolucent table extension assembly of FIG. 1.

FIG. 9 is a side view of the table extension of FIG. 8, but also showing an outboard stabilization device, in this case a skull clamp, secured to the tooling support outboard of the edge of the table extension.

FIG. 10 is a side view, similar to FIG. 9, showing the inboard horseshoe headrest tilted relative to the table extension assembly.

DETAILED DESCRIPTION OF THE INVENTION

Figure 1:
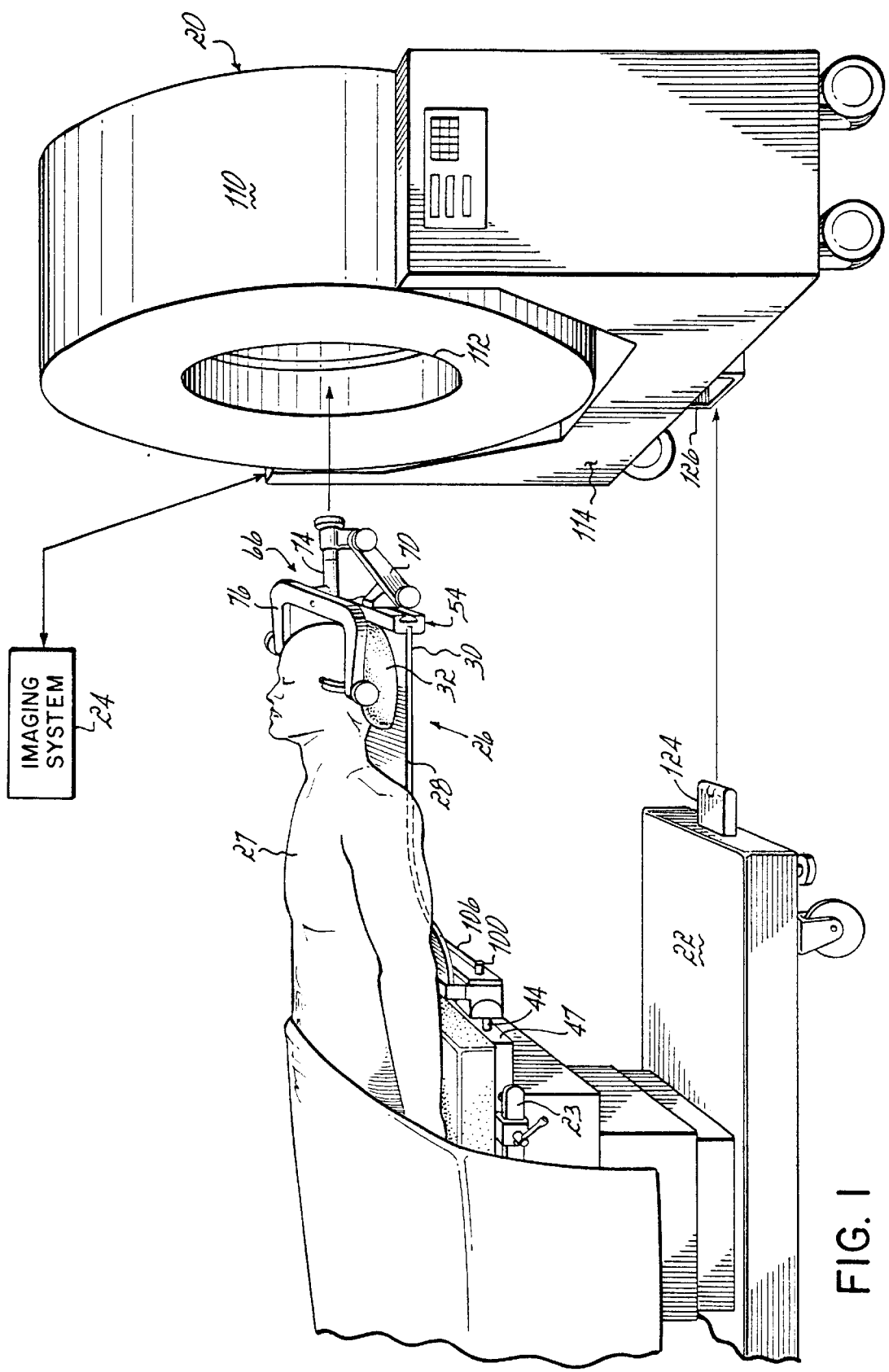
FIG. 1 is a perspective view of a portion of a surgical table including a radiolucent table extension assembly, in accordance with the general principles of the invention.

Referring to FIG. 1, a portable CT scanning system 20 is located in an operating suite with an operating table 22. The CT scanning system may be either a mobile system such as that commercially available from Analogic of Peabody, Mass. or a stationary scanning system such as that commercially available from General Electric Medical Systems of Milwaukee, Wis. The operating table 22 may be one of many commercially available tables, for example, an operating table commercially available from Amsco of Erie, Pa., MDT Diagnostic Co. of N. Charleston, N.C., or other suppliers. The operating table has a lateral rail 23 extending along each side of the table to which retractors, clamps and other devices maybe attached and stably supported. A stereotactic image processing system 24, for example, the MAYFIELD-ACCISS image processing system, commercially available from Ohio Medical Instrument Company, Inc. of Cincinnati, Ohio is operatively connected to the scanner 20 and responsive to scan data provided by the CT system 20, to provide selected images on a display screen of the scan data along selected planes. Use of an imaging system 24 of this type is described in U.S. Pat. No. 5,695,501, which is expressly incorporated by reference herein, in its entirety. To facilitate the use of the operating table 22 with the CT system 20, one end of the operating table is used to support a radiolucent table extension 26.

Figure 4:
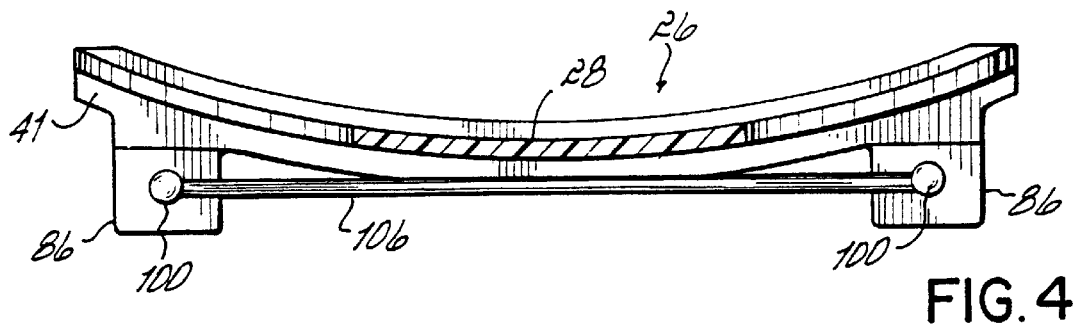
FIG. 4 is a cross-section view taken along the line 4—4 of FIG. 2.

Referring to FIG. 2, the table extension 26 includes a support member or plate 28 made of radiolucent material, for example, wood, carbon graphite, etc, and the table extension 26 has a length to normally support the upper torso and head of a patient 27, the upper torso being defined as the portion of the patient's body above the waist including the head. As shown in FIG. 4, the patient support member 28 has a curved cross-sectional profile and has a laminated construction with a center layer of mahogany between two outer layers of carbon graphite, although the invention also contemplates molding the member 26 as one integral piece. The curve is normally a circular arc having a relatively large radius, for example, 28 inches, to generally conform to the shape of a patient. The support member 28 may have a length up to about 52 inches, although most procedures can be accommodated with a shorter-length, such as 36 inches. The outer or distal end 30 of the support member 28 includes a horseshoe headrest 32 that is generally U-shaped and filled with a gel to comfortably and properly support the patient's head. The headrest 32 surrounds an opening 34 within the support member 28. The opening 34 is sized to receive the face of a patient lying on the support member 28 in a prone position. The distal end 30 is narrower than the inner or fixed end 36, and the narrow profile of the distal end 20 of the support plate 28 facilitates positioning the distal end 30 in scanner 20 even if the table or the scanner 20 is tilted. The support member 28, when viewed from the top as shown in FIG. 2, has a profile that flares outward from the distal end 30 to the fixed end 36. The width of the support member 28 at the fixed end 36 is generally greater than the distance between the holes 46 and is normally equal to the width of the operating table 22.

Figure 5:
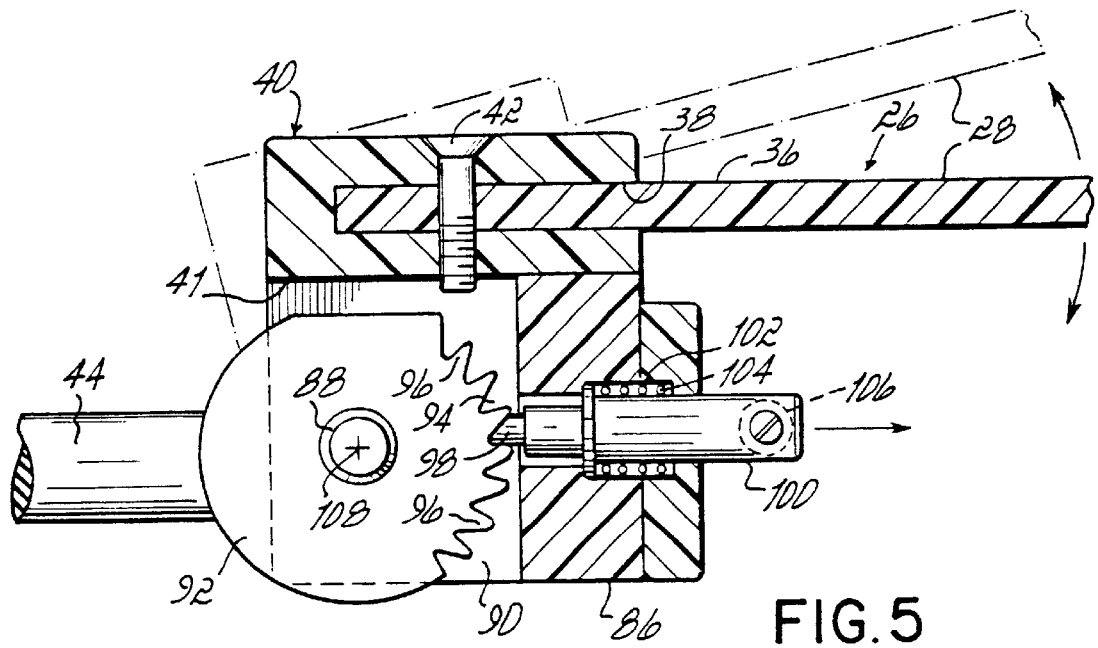
FIG. 5 is a cross-section of view taken along the line 5—5 of FIG. 2.

Referring to FIG. 5, the support member 28 is secured at its fixed end 36 within a slot 38 of an attachment base 40. Fasteners, for example, screws 42 are used to clamp and secure the support plate 28 within the attachment base 40. The attachment base 40 is mechanically linked to support shafts 44, which extend longitudinally from the fixed end of the support base 40 and are sized to fit into holes 46 of the table 22. Thus, the support plate 28 provides an extension of and is cantilevered from the end 23 of the table 22.

Referring to FIGS. 1–3, an instrument or tool support or rail 54 is attached to the periphery of the distal end 30 of the support plate 28. The tool support 54 may be made from a "DELRIN®" acetal polymer material, a polyethersuylfone ("PES") material or a carbon graphite. An inner directed side 56 of the tool support 54 includes a slot 58 for receiving the portion of the periphery 60 of the support plate 28. The support plate 28 may be secured in the slot 58 using fasteners or adhesives or both. The slot 58 is curved with respect to a radius sweeping a vertical plane that is generally perpendicular to and extends across the width of the support plate 28. An outer directed side 62 of the tool support 54 includes a second slot 64 that is generally parallel to a longitudinal center line of the tool support 54. Thus, when viewed from the end of the support plate 28, that is, looking to the left in FIG. 3, the slot 64 will appear generally as a straight slot. The slot 64 permits medical instruments, such as stabilization devices 66, for example a skull clamp, retractors, clamps, supports, etc., also collectively referred to as "tools" herein, to be supported, selectively moved with respect to the distal end 30 of the support plate 28 to desired positions and locked or secured in place. In the illustrated embodiment, the slot 64 has a dovetail shape that matches a mating dovetail on the tool to be mounted and secured to the tool support 54. For example, the tool support 54 may receive one end 68 of a transitional element 70. The other end 72 of the transitional element 70 is rotatably coupled to a swivel adaptor 74. The swivel adaptor, in turn, is coupled to a skull clamp 76. The skull clamp 76 is normally manufactured from radiolucent materials, for example, as described in U.S. Pat. No. 5,276,927 issued to the assignee of the present invention.

As shown in FIG. 3, the support plate 28 is often used in a generally horizontal position such that the top of the operating table 22 is generally in line with the support plate 28. However, numerous surgical procedures require that the support plate 28 be tilted or pivoted up or down with respect to the end 25 of the table 22. The tilting or pivoting of the support plate 28 is accomplished by the mechanism illustrated in FIG. 5. The attachment base 40 includes a pair of housings 86 connected to a lower surface 41 at a location near the ends of the attachment base 40 (FIG. 4). The attachment base 40 and housings 86 may be cast or made from aluminum. The support shafts 44 are rigidly connected at one end to respective cross-shafts 88 that are rotatably mounted within the lateral side walls 90 of the housings 86. The cross-shafts 88 extend through brass bushings (not shown) mounted in the lateral side walls 90 and function as pivot pin in a hinge. The support shafts 44 function as fixed hinge members, and the housings function as movable hinge members. A ratchet wheel 92 is fixed at the center of each of the cross-shafts 88, and each ratchet wheel has notches 94 between teeth 96. The support shafts 44, cross-shafts 88, and ratchet wheels 92 are normally made from stainless steel.

Pawls 98 are shaped to mate with and fit into the notches 94 of respective ratchet wheels 92. Each pawl 98 is mounted on the end of a release shaft 100 that extends through a bore 102 of a respective housing 86. With the pawls 98 in the position illustrated in FIG. 5, they function to securely support their respective housings 86 and the support plate 28 in a generally horizontal position. A spring 104 provides a bias to forcibly maintain the pawls 98 within the slots 94. The pawls 98 and release shafts 100 are normally made of stainless steel.

As shown in FIG. 4, a release shaft or bar 106, normally made of aluminum or stainless steel, extends between the shafts 100 and the housings 86. By pulling on the bar 106, the shafts 100 move to the right as viewed in FIG. 5; and the pawls 98 are pulled out of engagement with respective ratchet notches 94. Once the pawls 98 is disengaged from the notches 94, the support plate 28, attachment base 40, and housings 86 are freely rotatable relative to respective stationary ratchet wheels 92, cross-shafts 88 and support shafts 44. Thus, the support plate 28 may be pivoted with respect to an axis of rotation 108 in the generally clockwise or counter-clockwise direction until the support plate 28 is at its desired angular position as shown in phantom in FIG. 5. Normally, the support plate 28 may be pivoted approximately 60° above and below its illustrated horizontal position. When the bar 106 is released, the springs 104 push their respective pawls 98 into the closest ratchet notches 94, thereby securing the support plate with the desired angle or tilt.

In use, referring to FIG. 1, the scanning system 20 and operating table 22 are brought into a surgical suite. The scanning system 20 has a toroid shape scanning element 110 with a central opening 112 defining an enclosed or encircled scanning zone with which the portion of the patient to be scanned is axially aligned. The scanning element 110 further has the capability of rotating or tilting within its base 114 with respect to a diametric horizontal axis. The distal end 30 of the support plate 28 is narrowed so that it can extend into the opening 112 without interference. If necessary, the head section (not shown) of the table 22 is removed therefrom, and the radiolucent table extension 26 is mounted to the table by inserting the support bars 44 into mating bores 46 on the end surface 47 of the table 22. The patient 116 is then positioned on the table in a posture suitable for a surgical procedure. The length of the support plate 28 is sized such that the patient's upper torso and head are accessible for scanning and surgical procedures. The portion of the patient's anatomy on which the surgical procedure is to be performed may be stabilized by various clamps and restraining devices, for example, the skull clamp 76. Further, the support plate 28 or the scanning element 110 may be tilted so that the desired posture and/or scanning plane is achieved.

When the desired surgical posture is achieved, normally the patient will have already been scanned; and the surgical planning and procedure can be performed. Thereafter, a portion of the radiolucent table extension 26 is then moved into the opening 112, for a follow-up scan. The extent to which the extension 26 is moved into the opening 112 depends on what portion of the head or upper torso is to be scanned. The initial alignment of the table extension may be determined by visual inspection; and thereafter, a scan made to determine exactly whether and to what extent the table extension may be out of alignment. Alternatively, the scanner may be equipped with LED's or other sources of light providing beams of light with which the table extension can be aligned. In another embodiment, the table 22 may have an alignment tab 124 (FIG. 1) which is moved into an alignment slot 124 on the scanner 110. When the tab 124 is properly seated in the slot 126, the table is properly aligned with the scanner 110. The scanning process is executed by the scanning machine moving the scanning element 110 incrementally in an axial direction and with each increment, a scan is taken. Thereafter, the extension 26 and the patient are removed from within the scanning element 110, either by moving the scanning machine 20 or the operating table 22. The scan data is then used in association with the imaging systems 24 to plan the surgical procedure. The surgical procedure is then performed, and thereafter, the patient may be moved back into the scanning machine 20, and the scanning process repeated. The scanning and imaging system maybe used to gauge the effectiveness of the surgical procedure; and if necessary, further procedures performed. The above process may be executed any number of times with the patient remaining in the desired position on the same patient support.

Thus, the above-described operating table and radiolucent table extension has a significant advantage of not only being able to support a patient during a scanning process, but also support the patient in the identical posture during a surgical procedure. The radiolucent table extension permits an operating table that is normally nonradiolucent and inappropriate for scanning purposes to be used with a scanning machine. Further, the table extension may be tilted to accommodate different desired surgical postures and is sized and shaped to readily fit within the opening of a scanning element, whether in a horizontal or tilted position. Further, not only does the table position permit successive scanning and operative procedures on the upper torso and head of a patient, but the radiolucent table extension 26 readily supports the patient in a prone, or supine position.

Figure 6:
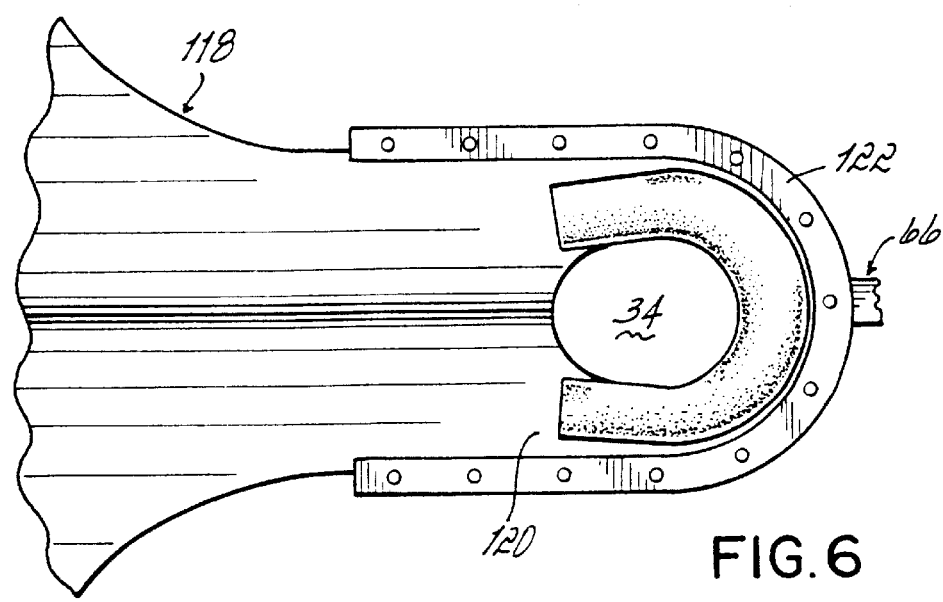
FIG. 6 is a top plan view of an alternative embodiment of the radiolucent table extension assembly in accordance with the general principles of the invention.
Figure 7:
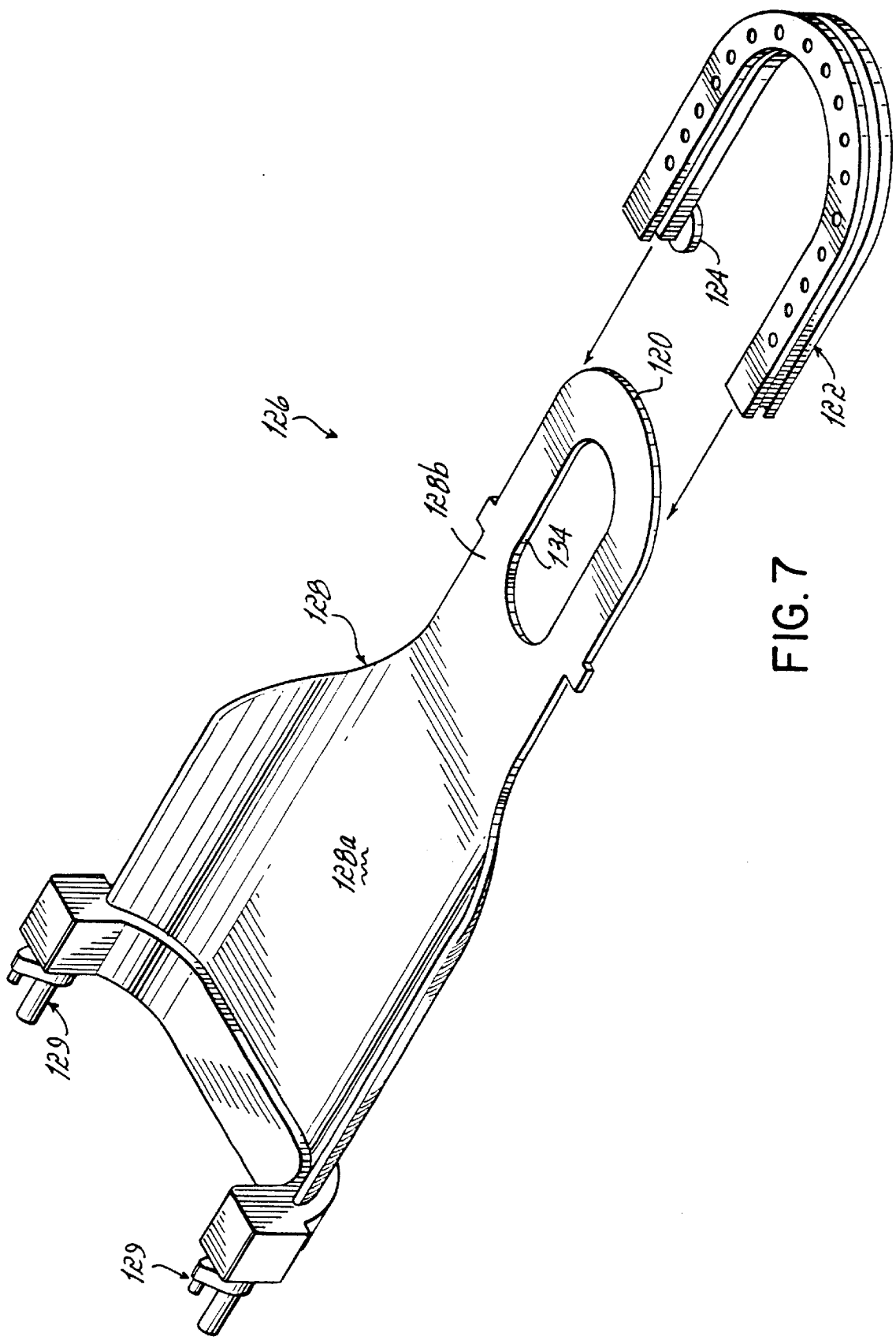
FIG. 7 is a perspective view of yet another alternative embodiment of a table extension assembly in accordance with the general principles of the invention.

Referring to FIG. 6, an alternative embodiment of the support plate 118 has an distal end 120 that is curved to generally follow the profile of the headrest 32. Further a tool support 122 extends along the periphery of the support plate 118 to a location at which the width of the support plate 118 begins to flare outwardly toward the width of the fixed end 32. Other than its length, the construction and function of the tool support 122 is substantially identical to the tool support 54 described earlier.

Figure 8:
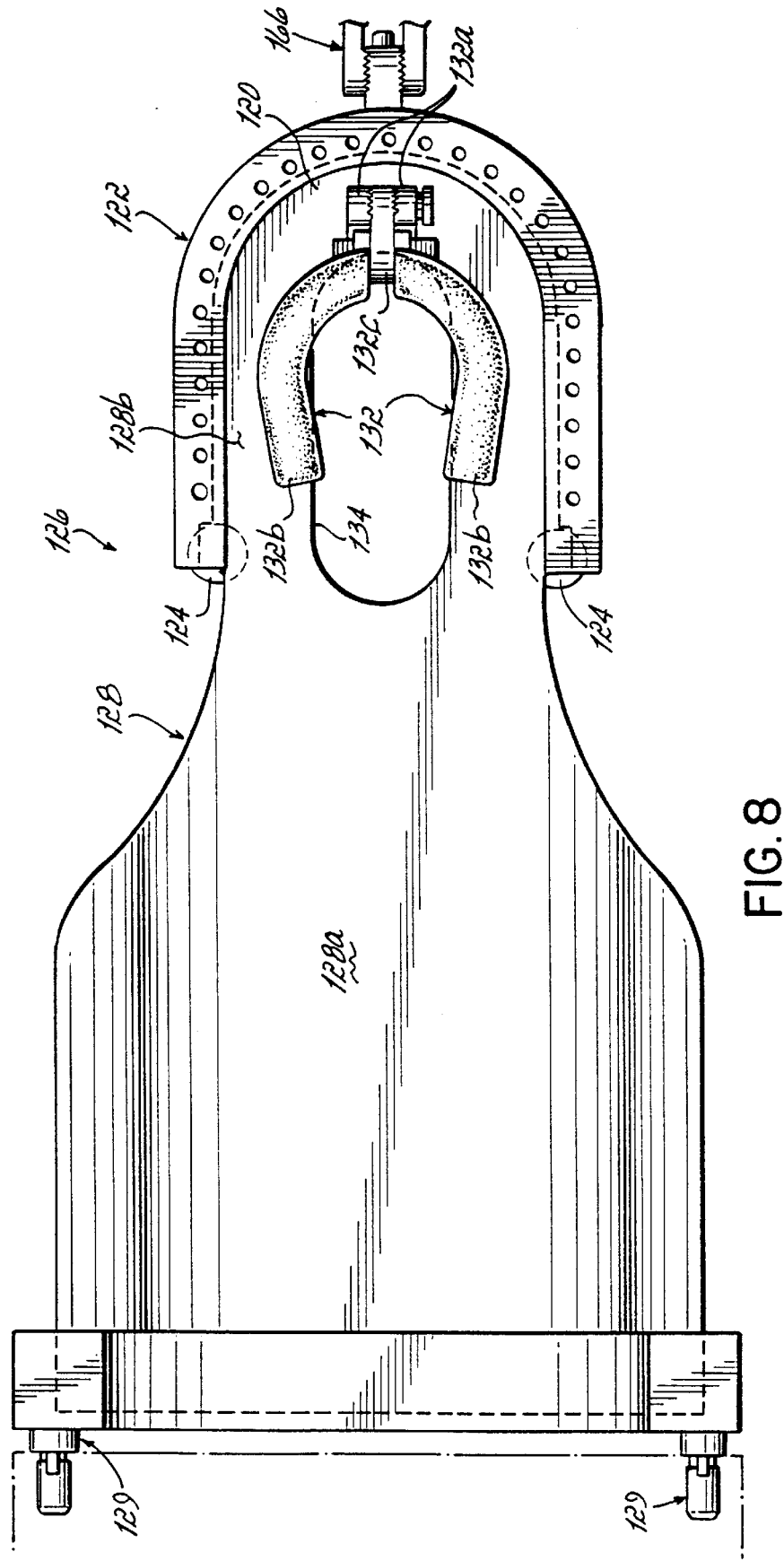
FIG. 8 is a top plan view of the table extension assembly shown in FIG. 7, but with additional hardware shown, namely an inboard horseshoe headrest.

According to a further variation of this embodiment, as shown in FIGS. 7–10, a radiolucent table extension assembly 126 includes a tool support 122 removably connected to the peripheral edge at a distal end 120 of the support member 128. The support member 128 is preferably pivotal relative to a table (not shown) to which is connected. This is done by incorporating a pivot mechanism (not shown) into the table extension assembly 126 or even into the table itself, as with surgical tables commercially available from Midmark of Dayton, Ohio, which are built so as to tilt relative to horizontal. With such tube, the support member 128 is simply plugged via pins 129 into the table (not shown) which is already oriented at a desired angle. The support member 128 may have an inner portion 128a which is contoured to the body of the patient and an outer portion 118b which is generally flat. The tool support 122 may removably secure to the support plate 128 via a pair of hand-tightenable knobs 124. The member 128 includes an opening 134, and a radiolucent horseshoe headrest 32 or 132 resides inboard of, and generally in alignment with, a portion of the opening 134 as shown in FIGS. 8–10. This configuration enables a bag-like surgical drape (not shown) to be placed over a patient who is supported on the support member 128 by the horseshoe 132, and in an intubated condition, and then the tool support 122 connected to the distal end 120 to confine the drape within the edge of the support member 128, between the support member 128 and the tool support 122. Phantom line 130 in FIG. 9 illustrates an example of where this drape would be located. The patient 27 may be supported on the support member 128 in a face up or face down position. In a face down position, the hole 134 may be used for routing of one or more intubation tubes (not shown) or other medical instruments to the patient 27.

This results in locating the tool support 122 outside the drape 130, in the surgical field. This is also true for any other attendant hardware or assembly components 166 connected thereto, such as a skull clamp 174. For some types of surgical procedures, this draping arrangement may be preferable during surgical or scanning procedures. At least with respect to scanning, this configuration helps to assure that no structure will impede movement of the table extension assembly 126 into the scanning zone.

With this embodiment, i.e., the tool support 122 and the outer stabilization device 166, in this case the skull clamp 174, connected "outboard" of the outer edge of the support member 128, it is also possible to hold the head of the patient with a removably connected, tiltable horseshoe 132 located inboard of the edge of the support plate member 128 (FIGS. 8, 9). FIG. 10 shows the headrest 132 tilted relative to the support member 128. With the tiltable horseshoe headrest 132, there is a first connection piece 132a which mounts to an inside edge of the opening 134 and a pair of mirror image headrest pieces 132b and 132c (FIG. 8) which connect to each other in a common plane and tilt relative to the piece 132a. This tilting feature gives the surgeon additional versatility in positioning the patient. Both the connector piece 132a and the second headrest pieces 132b and 132c are made of radiolucent material so as to not create artifacts during scanning.

FIGS. 8–10 show outer tooling 166, specifically a skull clamp 174, along with an inner device such as a horseshoe headrest 132 connected to the tool support 122. Preferably the tooling or devices 166 are radiolucent and positively hold the patient in a fixed position relative to the support member 128, so that the patient remains in a desired position during successive surgery and scanning procedures. This is done with the inboard headrest 132 and/or an outer stabilization device 166, to affirmatively hold the patient 27 in a fixed position relative to the support plate 118. This structural capability facilitates convenient positioning of the patient 27 during successive scanning or surgical procedures, thereby enabling the surgeon to conveniently and easily perform follow-up procedures.

As will be appreciated, the horseshoe-shaped gel filled headrest 32 illustrated and described may have other embodiments. For example, the headrest may be circular or another shape, may be filled with a different material, or may be thicker so that the patient's head is supported fully above the upper surface of the support plate 28. The headrest 132 shown in FIGS. 8–10 represents only one of these possible variations. Further, the opening 34 may have other configurations. For example, the opening 34 may be replaced by, or supplemented by, one or a plurality of holes of any shape for various purposes, for example, ventilating the patient, access for tubes and other equipment, drainage, or openings through which the patient can see or the patient's eyes can be seen. As will be appreciated, separate inserts or built-in hole covers may be used to fill or cap the holes when they are not being used.

Figure 11:
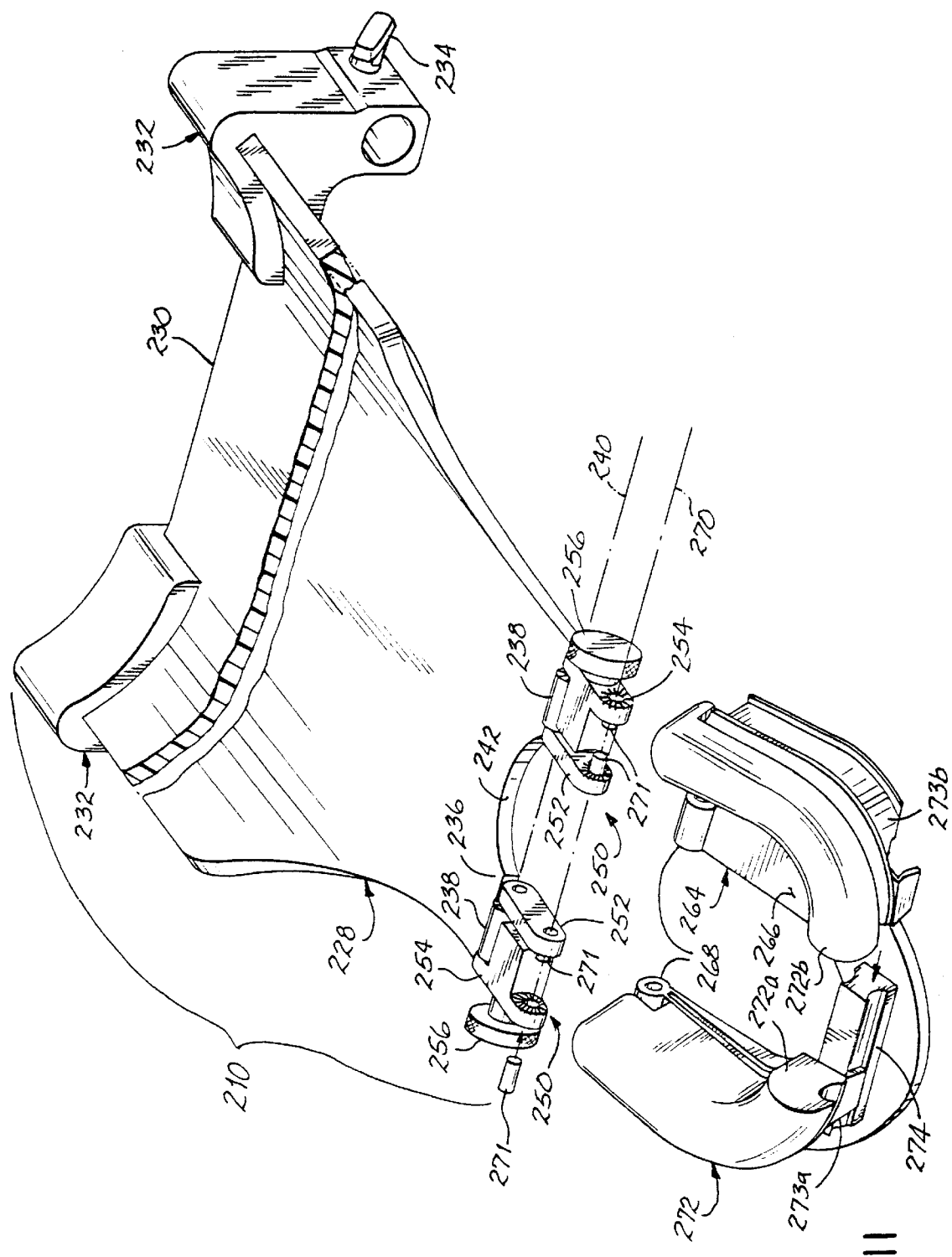
FIG. 11 is a disassembled perspective view of a radiolucent table extension and double-hinged radiolucent adaptor assembly in accordance with a preferred embodiment of the present invention, using a radiolucent horseshoe headrest as the patent stabilization device.
Figure 12:
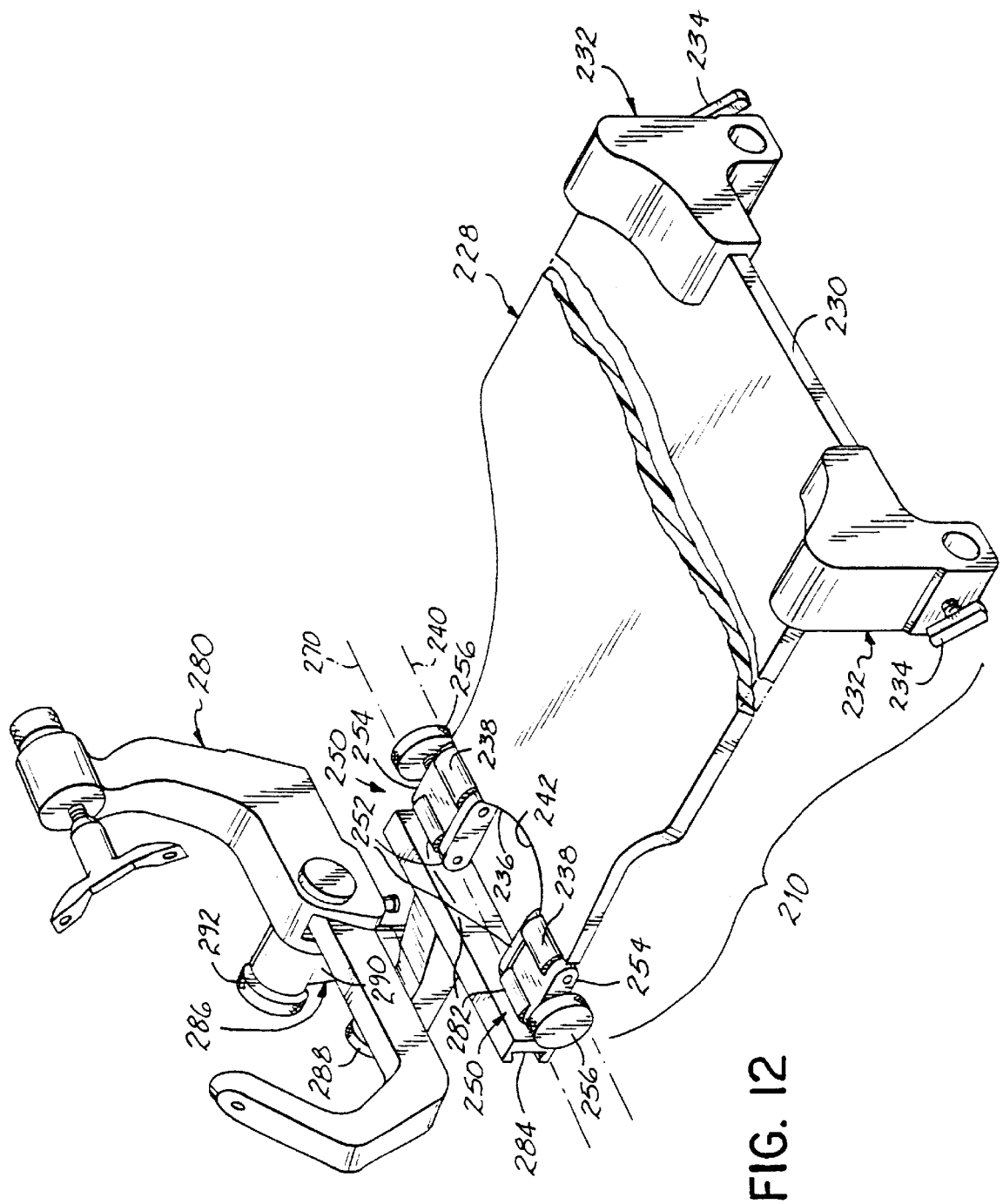
FIG. 12 is a another perspective view of a radiolucent table extension and double-hinged radiolucent adaptor assembly, in accordance with a preferred embodiment the present invention, with a radiolucent skull clamp serving as the patient stabilization device.
Figure 13:
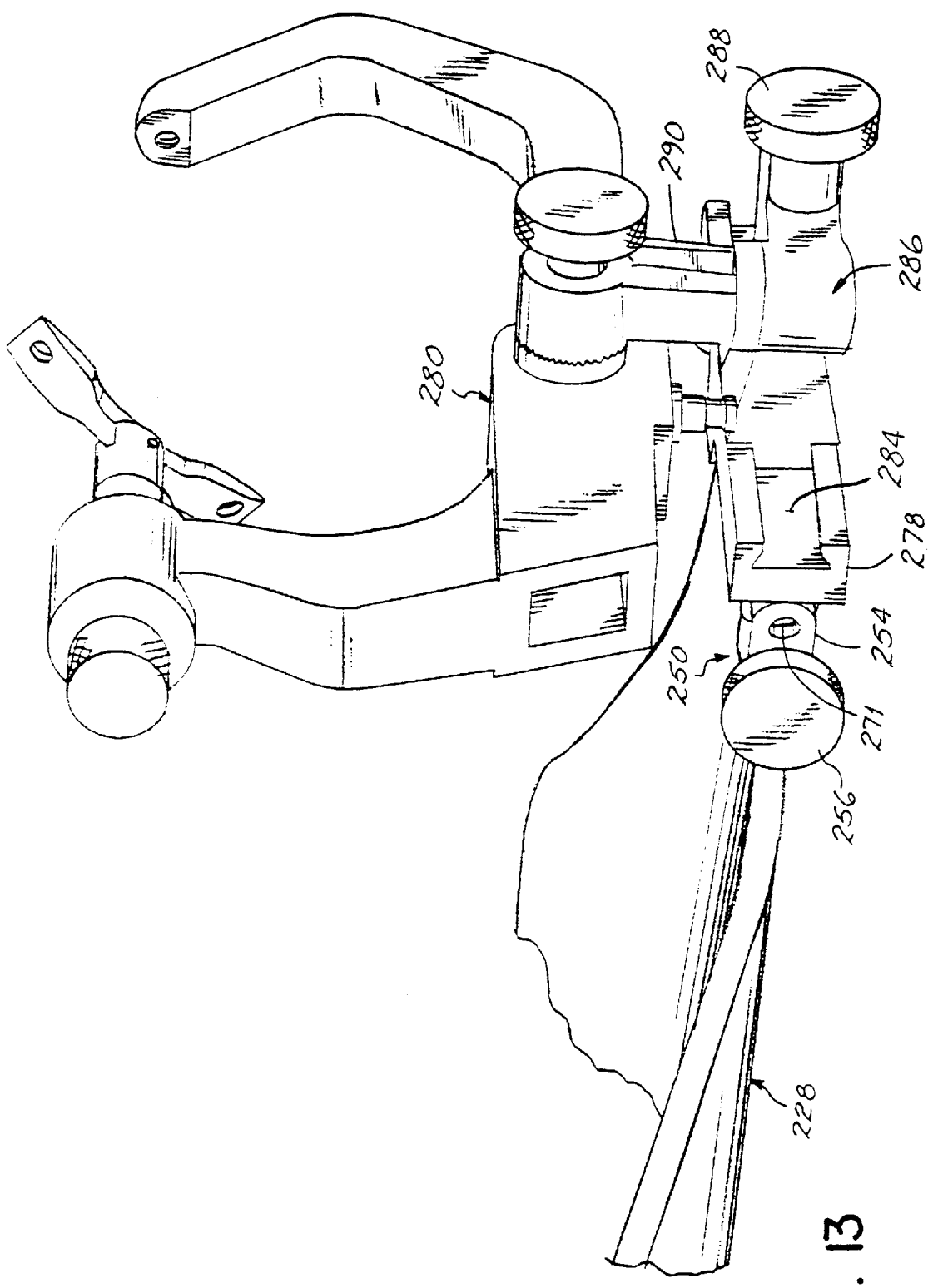
FIG. 13 is a fragmentary view of one of the radiolucent adaptor sub-assemblies according to a preferred embodiment of the present invention.

In accordance with a preferred embodiment of the present invention, FIGS. 11–13 show a radiolucent hinged adaptor assembly 210 and a radiolucent table extension 228. More particularly, the radiolucent table extension 228 is adapted to support the upper torso of a patient, with the rest of the patient supported by a surgical table 22 of the type shown in FIG. 1. As shown in FIG. 11, a first, or inboard, end 230 of the table extension 228 connects to the surgical table 22. Preferably this connection at the first end 230 occurs via a pair of spaced base mounts 232. Each of the base mounts 232 engages an inboard corner of the radiolucent table extension 228 and is shaped to receive an outwardly extending post or bar (not shown) extending from the surgical table 22. A threaded knob 234 tightens upon the inserted post on both sides of the surgical table 22, to securely mount the extension 228. Preferably, the extension 228 comes in two different lengths. Depending on the length of the extension 228 and the type of table 22, the manner of mounting the extension 228 may vary.

A second or outboard end 236 of radiolucent table extension 228 includes a pair of spaced collars 238 aligned along a first connection axis 240. The first connection axis 240 is oriented horizontally and perpendicular to the longitudinal direction of the radiolucent table extension 228. Between the spaced collars 238, the radiolucent table extension 228 includes an arcuate cutout region 242. The first connection axis 240 provides for hinged, or pivotal, movement of the radiolucent adaptor assembly 210, and everything else connected thereto, relative to the radiolucent table extension 228.

To provide this hinged movement about first connection axis 240, the radiolucent adaptor assembly 210 actually comprises a pair of spaced adaptor subassemblies 250, each of the adaptor subassemblies 250 associated with one of the spaced collars 238 of the table extension 228. Each subassembly 250 includes an interior piece 252 and an exterior piece 254 which are tightenable in a horizontal direction via a threaded knob 256. The threaded knob 256 includes a screw (not shown) which extends through an oversized central bore (not shown) in exterior piece 254 and threads within a complementary shaped, internally threaded recess (not shown) located within interior piece 252.

As shown in FIG. 11, the exterior piece 254 is T-shaped, while the interior piece 252 is uniform in thickness. If desired, this arrangement can be switched around, with the interior piece 252 being T-shaped and the exterior piece 254 being uniformly thick, so long as the interior piece 252 and exterior piece 254 are tightenable together upon the respective collars 238. This would also require switching the threaded and the through holes.

Along first axis 240, the interior piece 252 and the exterior piece 254 have aligned openings machined therein which receive locator pins, via a press fit. The locator pins are sized to extend into the collar 238 along the connection axis 240, with a slip fit, so as to be rotatable relative to the collar 238. Together, the opposing locator pins of the interior piece 252 and the exterior piece 254 are held by the collar 238 along the first connection axis 240, so that upon tightening of threaded knob 256 the inwardly directed surfaces of the interior piece 252 and the exterior piece 254 engage the outwardly directed surfaces of the collar 238. Preferably, the outwardly directed surfaces of the collar 238 are serrated, or have a starburst configuration, and the inwardly directed surfaces of the interior piece 252 and the exterior piece 254 likewise have correspondingly shaped serrations.

Thus, upon sufficient tightening of threaded knob 256, the interior piece 252 and exterior piece 254 will move together horizontally until their respective engagement surfaces contact and engage opposing surfaces of the collar 238. This engagement force holds the radiolucent adaptor subassembly 250 in a fixed position relative to the radiolucent table extension 228. Upon loosening the threaded knob 256, the subassembly 250 may be hingedly moved relative to first connection axis 240 to a different position, whereupon the threaded knob 256 may again be tightened to form a rigid connection.

FIG. 11 also shows a radiolucent support 264 which connects to the radiolucent adaptor assembly 210. More specifically, in the arrangement shown in FIG. 11, the radiolucent support 264 is a U-shaped panel 266 which has a pair of spaced collars 268 which connect to the spaced subassemblies 250 along the second connection axis 270. The structure and manner of connecting the radiolucent support 264 (in this case a U-shaped panel 266) relative to the adaptor assembly 210 along second connection axis 270 are similar to that which has been aLready described with respect to the connection of the adaptor assembly 210 to the table extension 228 along the first connection axis 240. That is, outwardly directed surfaces of the collars 268 are serrated. Upon tightening of knob 256 to move the interior piece 252 and the exterior piece 254 toward each other in a horizontal direction, these pieces 252 and 254 engage the outwardly directed surfaces of the collar 268 to connect the panel 266 to the adaptor assembly 210 in a desired position relative to the second connection axis 270.

Preferably, the threaded knobs 256 on both sides of the table extension 228 are tightened or loosened in unison, to facilitate orienting the radiolucent support 264 relative to the table extension 228 in a coordinated fashion. As with the connections along the first connection axis 240, along the second connection axis 270 each adaptor subassembly 250 includes opposing locator pins 271 which extend along the second axis 270 and into the collars 268, to locate the interior and exterior pieces 252 and 254 in a desired position relative to the second axis 270.

In FIG. 11, the hinged adaptor assembly 210 of the present invention advantageously interconnects a horseshoe headrest 272 to the table extension 228, in a manner such that the horseshoe headrest 272 can be tilted relative to the table extension 228 about the first connection axis 240, tilted about the second connection axis 270, or both. Preferably, the horseshoe headrest 272 includes an upstanding mount 274 oriented perpendicular the longitudinal axis of the table extension 228. This mount 274 may include a dovetail shape, or any other desired cross-sectional shape for that matter, which corresponds to a complementary shape formed in a headrest portion 272a or 272b, so that the headrest portions 272a and 272b can be slidably located on the mount 274.

If desired, each of the horseshoe headrest portions 272a and 272b may include a base 273a and 273b made of radiolucent material (of the type used to make support 54), for supporting the cushion thereabove along its curved length. The base 273a and 273b may be made of the same material as the panel 266 and the mount 274. With this construction, the headrest itself 272 comprises a pad or cushion secured to the base 273a and 273b.

Notably, when the adaptor assembly 210 of the present invention is used in conjunction with the horseshoe headrest 272, the U-shaped panel 266 combines with the arcuate cutout region 242 to form an enclosed oval. The oval is bisected by the first connection axis 240 and by the second connection axis 270, and an outermost end of the entire assembly is now defined by the outermost end of the U-shaped panel 266. Thus, the headrest 272 resides inboard of the outermost end of panel 266, and in effect, the adaptor assembly 210 provides a pair of intermediately located hinged axes 240 and 270 for locating the horseshoe headrest 272 in a desired position relative to the table extension 228 and the patient supported thereon.

Because of the versatile design of the radiolucent adaptor assembly 210 of the present invention, the U-shaped panel 266 may be hinged downwardly with respect to table extension 228 about first connection axis 240, downwardly about second connection axis 270, or both, or upwardly relative to one or both of these spaced parallel axes 240 and 270, or even upwardly with respect to one of the axes 240 or 270 and downwardly with respect to the other. Moreover, this versatility is achieved via tightening and loosening of a single pair of aligned and spaced knobs 256, preferably with the entire cantilevered assembly held temporarily in a desired position during the tightening or loosening. In effect, the knobs 256 are actuator mechanisms for locking the patient stabilization device in a desired position relative to the table extension 228, and the actuators are aligned along an axis which resides between the first axis 240 and the second axis 270

FIGS. 12 and 13 show the radiolucent adaptor assembly 210 of the present invention in a configuration wherein the radiolucent support 264 more specifically comprises a radiolucent bracket 278 which is adapted to hold a radiolucent skull clamp 280. As with the U-shaped panel 266, the radiolucent bracket 278 includes a pair of spaced collars 282 which are adapted to be connected to the spaced adaptor subassemblies 250 along the second connection axis 270. This likewise enables the skull clamp 280 to be oriented in a desired position relative to the table extension 228, via hinged movement about first connection axis 240, hinged movement about second connection axis 270, or both.

Because of the versatility provided by this radiolucent adaptor assembly 210, the structure used for interconnecting the skull clamp 280 to the radiolucent bracket 278 may also be simplified. More specifically, as shown in FIG. 13, the radiolucent bracket 278 includes an internal dovetail 282 sized to receive a complementarily shaped member from an intermediate connector 286, the connector 286 being lockable to the radiolucent bracket 278 via an adjustment knob 288 and further including an upstanding member 290 which retains another adjustment knob 292 which tightens a starburst connection of the intermediate connector 286 to the skull clamp 280.

As with the horseshoe headrest 272, when using a radiolucent skull clamp 280 with the present invention, the radiolucent adaptor assembly 210 provides two parallel axes of connection 240 and 270 residing between the radiolucent table extension 228 and the patient stabilization device used to hold the head of the patient in a desired position. Thus, the present invention increases the versatility of patient positioning relative to a radiolucent table extension assembly, for advantageous use in interoperative scanning procedures. This versatility is available for patient stabilization with either a skull clamp or a horseshoe headrest. In fact, this invention makes it easy for attendants to interchange the surgical set up, by removing one of these two different holding devices and connecting the other. Moreover, the present invention achieves these advantages in a manner which is user-friendly for the surgeon and operating room attendants, because the maneuverability of the patient stabilization device is achieved about two spaced parallel axes 240 and 270 via adjustment of a pair of spaced adjustment knobs 256.

The interior pieces 252, the threaded knobs 256 and the locator collars 238 and 268 along the first connector axis 240 and the second connector axis 270 are made by Potts Composites of Floydada, Tex. out of carbon fiber composite and epoxy resin material. The extension 228 is made by MTD Inc. of Andover, N.J. out of "Delrin®" acetyl polymer material. If desired, each collar 238 and 268 may include an internal sleeve (not shown) made of hydlar-kevlar. The exterior pieces 254 are made out of the same material described above with respect to support 54. However, it will be understood by those skilled in the art that these various components may be made of any suitably rigid radiolucent material.

Also, the table extension 228 may receive a radiolucent foam pad (not shown) thereon in order to comfortably support a patient.

In another related aspect of the invention, a target holder and its attendant components and/or an articulated arm, as shown in FIG. 3 of U.S. Pat. No. 5,695,501, may be removably connectable to the one or more radiolucent patient stabilization devices and/or the radiolucent tool support, so that the target holder and its components and/or the articulated arm may be disconnected prior to scanning and then affirmatively reconnected in the exact same position after scanning. This is important because the target holder and its components and/or articulated arm are typically not radiolucent. Therefore it is undesirable to keep them connected to the rest of the structure during scanning. These components could create artifacts or impede movement of the patient into and out of the scanning zone. Yet, it is also important to reconnect in the same relative position. This assures that, after scanning, the viewing probe or the surgical device (both of which are removably held along a line of sight by the target holder) will be aligned and located in the same position relative to the patient as before the scanning procedure.

Therefore, the invention in its broadest aspects is not limited to the specific details shown and described. Consequently, departures may be made from the details described herein without departing from the spirit and scope of the claims which follow.

I claim:

1. A surgical table extension assembly for use in combination with a surgical table having opposed longitudinal ends and a scanning machine having an enclosed scanning zone, comprising:

a radiolucent member having an inboard first end adapted to be removably attached to one of the longitudinal ends of the table and to extend outward from the longitudinal end in cantilever fashion, the radiolucent member having a rigidity sufficient to support an upper torso and the head of a patient with the patient being further supported by an adjacently located surface of the table, the table and the radiolucent member being movable relative to the scanning machine to locate the member and the head of the patient within the scanning zone;

a radiolucent adaptor assembly hingedly connected to an outboard second end of the member along a first connection axis;

a radiolucent support hingedly connected to the radiolucent adaptor assembly along a second connection axis with an opening residing between the radiolucent support and the radiolucent member; and at least one radiolucent patient stabilization device supported on the radiolucent support and adapted to stabilize the head of the patient, the first connection axis and the second connection axis providing increased versatility in locating the patient stabilization device in a desired position relative to a patient, the opening providing for advantageous routing of tubing to the patient.

2. The surgical table extension assembly of claim 1 wherein the outboard second end of the radiolucent member includes a pair of spaced collars aligned along a first connection axis, the radiolucent adaptor assembly being removably connected to the radiolucent member at the spaced collars and hingable about the first connector axis relative to the radiolucent member.

3. The surgical table of claim 1 wherein the outboard second end of the radiolucent member includes an arcuate central cutout region, thereby defining the opening between the member and the radiolucent support.

4. The surgical table of claim 1 wherein the radiolucent adaptor assembly comprises two spaced radiolucent adaptor subassemblies.

5. The surgical table of claim 1 wherein the radiolucent support includes a pair of spaced support collars aligned along a second connection axis, the radiolucent adaptor assembly being removably connected to the radiolucent support at the spaced support collars and hingable about the second connector axis relative to the radiolucent support.

6. The surgical table of claim 1 wherein the radiolucent support is a U-shaped radiolucent panel and the patient stabilization device is a horseshoe-shaped radiolucent headrest mounted on the radiolucent panel.

7. The surgical table of claim 6 and further comprising:
a radiolucent slide mount secured to the panel, the horseshoe-shaped radiolucent headrest comprising two separate radiolucent sections slidably secured on the radiolucent slide mount.

8. The surgical table of claim 1 wherein the radiolucent support is a radiolucent bracket and the patient stabilization device is a radiolucent skull clamp supported by the radiolucent bracket.

9. The surgical table of claim 8 further comprising:
a radiolucent intermediate connector secured to the radiolucent bracket, the radiolucent skull clamp secured to the radiolucent intermediate connector.

10. The surgical table extension assembly of claim 1 wherein the first and second connection axes are parallel.

11. The surgical table extension assembly of claim 1 wherein the patient stabilization device is hingably positionable relative to the radiolucent member about both the first and second connection axes and lockable into a fixed position via actuation of at least one actuator knob aligned along an actuation axis residing between the first connection axis and the second connection axis.

12. The surgical table extension assembly of claim 11 wherein actuation occurs via rotatable actuation of at least two spaced knobs aligned along the actuation axis and located on opposite sides of the opening.

13. A surgical table extension assembly for use in combination with a surgical table having opposed longitudinal ends and a scanning machine having an enclosed scanning zone, comprising:

a radiolucent member having an inboard first end adapted to be removably attached to one of the longitudinal ends of the table and to extend outward from the end in cantilever fashion, the radiolucent member having a rigidity sufficient to support an upper torso and the head of a patient with the patient being further supported by an adjacently located surface of the table, the table and the radiolucent member being movable relative to the scanning machine to locate the member and the head of the patient within the scanning zone;

a radiolucent adaptor assembly hingedly connected to an outboard second end of the member along a first connection axis;

a radiolucent support hingedly connected to the radiolucent adaptor assembly along a second connection axis; and a radiolucent horseshoe headrest supported on the radiolucent support and residing inboard of an outermost end of the radiolucent support, the horseshoe headrest adapted to stabilize the head of the patient, the radiolucent horseshoe headrest being pivotal about the first connection axis and the second connection axis relative to the radiolucent member, thereby to increase versatility in locating the patient stabilization device in a desired position.

14. The surgical table extension assembly of claim 13 wherein the radiolucent adaptor assembly comprises a pair of spaced adaptor subassemblies which partially define an enclosed oval.

15. In combination, the invention comprising:

a patient table having an upper support surface and opposed longitudinal ends the patient table and upper support surface including a radiolucent table extension assembly adapted to support a head and upper torso of a patient residing in a prone position on the upper support surface, the radiolucent table extension assembly cantilevered from one of said longitudinal ends of said table to extend outward of said longitudinal end and sized to be received within a toroidal shaped scanning zone of a scanning machine, the patient table and the radiolucent table extension assembly being movable relative to the scanning machine to locate the radiolucent table extension assembly within the scanning zone, and the radiolucent table extension assembly further comprising:

a radiolucent adaptor assembly hingedly connected to an outboard second end of the member along a first connection axis;

a radiolucent support hingedly connected to the radiolucent adaptor assembly along a second connection axis with an opening residing between the radiolucent support and the radiolucent member; and at least one radiolucent patient stabilization device supported on the radiolucent support and adapted to stabilize the head of the patient, the first connection axis and the second connection axis providing increased versatility in locating the patient stabilization device in a desired position relative to a patient, the opening providing for advantageous routing of tubing to the patient.

* * * * *

UNITED STATES PATENT AND TRADEMARK OFFICE
CERTIFICATE OF CORRECTION

PATENT NO.    : 6,557,195 B2
DATED         : May 6, 2003
INVENTOR(S)   : Charles E. Dinkler It is certified that error appears in the above-identified patent and that said Letters Patent is hereby corrected as shown below:

Column 1,
Line 36, "maybe" should be -- may be --.

Column 4,
Line 55, "surgery, a subsequent" should be -- surgery, subsequent --.

Column 5,
Line 21, "FIG. 3" should be moved to next line and indented.
Line 49, "patent" should be -- patient --.
Line 50, "is a another" should be -- is another --.
Line 52, "embodiment the" should be -- embodiment of the --.

Column 6,
Line 6, "maybe" should be -- may be --.
Line 34, "shorter-length" should be -- shorter length --.

Column 7,
Line 62, "is" should be -- are --.

Column 8,
Line 60, "maybe" should be -- may be --.

Column 9,
Line 14, "an" should be -- a --.
Line 27, "which is" should be -- which it is --.
Line 38, "removably secure" should be -- be removably secured --.

Column 11,
Line 63, "aLready" should be -- already --.

Column 13,
Line 2, "270" should be -- 270. --.

UNITED STATES PATENT AND TRADEMARK OFFICE
CERTIFICATE OF CORRECTION

PATENT NO.     : 6,557,195 B2
DATED          : May 6, 2003
INVENTOR(S)    : Charles E. Dinkler It is certified that error appears in the above-identified patent and that said Letters Patent is hereby corrected as shown below:

<u>Column 16,</u>
Line 22, "ends the" should be -- ends, the --.

Signed and Sealed this

Twelfth Day of August, 2003

JAMES E. ROGAN
*Director of the United States Patent and Trademark Office*